United States Patent
Weber

(10) Patent No.: US 9,078,650 B2
(45) Date of Patent: Jul. 14, 2015

(54) HANDLE SYSTEM FOR SUTURE DRIVING DEVICE

(75) Inventor: Robert McGregor Weber, Chino Hills, CA (US)

(73) Assignee: ARTHREX, INC., Naples, FL (US)

( * ) Notice: Subject to any disclaimer, the term of this patent is extended or adjusted under 35 U.S.C. 154(b) by 1427 days.

(21) Appl. No.: 11/286,923

(22) Filed: Nov. 23, 2005

(65) Prior Publication Data

US 2007/0118150 A1     May 24, 2007

(51) Int. Cl.
```
A61B 17/10    (2006.01)
A61B 17/04    (2006.01)
A61B 17/062   (2006.01)
A61B 17/28    (2006.01)
A61B 17/29    (2006.01)
A61B 17/06    (2006.01)
```

(52) U.S. Cl.
CPC .......... *A61B 17/0482* (2013.01); *A61B 17/062* (2013.01); *A61B 17/0469* (2013.01); *A61B 17/2833* (2013.01); *A61B 17/29* (2013.01); *A61B 2017/06028* (2013.01); *A61B 2017/2925* (2013.01)

(58) Field of Classification Search
CPC ........... A61B 17/0469; A61B 17/0482; A61B 17/062
USPC ......... 606/139, 144, 205, 147, 148, 170, 150; 81/300, 302
See application file for complete search history.

(56) References Cited

U.S. PATENT DOCUMENTS

| | | | |
|---|---|---|---|
| 1,293,565 A * | 2/1919 | Smit | 606/144 |
| 3,190,155 A * | 6/1965 | Ortman | 81/379 |
| 4,664,306 A * | 5/1987 | Levy | 227/67 |
| 4,890,615 A | 1/1990 | Caspari et al. | |
| 5,020,399 A * | 6/1991 | Annis et al. | 81/358 |
| 5,060,543 A * | 10/1991 | Warheit | 81/409 |
| 5,140,876 A * | 8/1992 | Fields | 81/408 |
| 5,176,702 A * | 1/1993 | Bales et al. | 606/208 |
| 5,190,560 A * | 3/1993 | Woods et al. | 606/137 |
| 5,286,255 A * | 2/1994 | Weber | 604/22 |
| 5,351,584 A * | 10/1994 | Warheit | 81/407 |
| 5,382,254 A * | 1/1995 | McGarry et al. | 606/143 |
| 5,449,365 A * | 9/1995 | Green et al. | 606/142 |
| 5,454,823 A | 10/1995 | Richardson et al. | |
| 5,613,977 A * | 3/1997 | Weber et al. | 606/170 |
| 5,810,848 A * | 9/1998 | Hayhurst | 606/144 |
| 5,938,685 A * | 8/1999 | Giurtino | 606/208 |
| 5,964,772 A * | 10/1999 | Bolduc et al. | 606/142 |
| 6,117,158 A * | 9/2000 | Measamer et al. | 606/208 |

(Continued)

*Primary Examiner* — Kathleen Holwerda
*Assistant Examiner* — Sarah Simpson
(74) *Attorney, Agent, or Firm* — Akerman LLP; Michael K. Dixon

(57) ABSTRACT

A handle system usable for controlling medical devices, such as suture delivery devices. In at least one embodiment, the handle system may be directed to an embodiment configured to be used with a suture delivery device. The handle system may enable a suture delivery system of the suture delivery device to be partially actuated to prevent a needle from falling out of the suture delivery device. The needle and components of the handle system may be held in position through use of a position retention arm. By preventing the needle from falling out of the suture delivery device, the efficiency and safety of a medical device to which the handle system is attached is greatly increased. In addition, surgical personnel using a medical device incorporating the handle system are able to use the medical device in any position without risk of the needle falling out.

21 Claims, 3 Drawing Sheets

(56) References Cited

U.S. PATENT DOCUMENTS

| | | | |
|---|---|---|---|
| 6,327,943 B1* | 12/2001 | Wrigley et al. | 81/413 |
| 6,905,057 B2* | 6/2005 | Swayze et al. | 227/176.1 |
| 7,118,587 B2* | 10/2006 | Dycus et al. | 606/205 |
| 7,223,272 B2* | 5/2007 | Francese et al. | 606/143 |
| 2002/0099388 A1* | 7/2002 | Mayenberger | 606/139 |
| 2002/0138084 A1* | 9/2002 | Weber | 606/139 |
| 2003/0023249 A1* | 1/2003 | Manetakis | 606/139 |
| 2003/0105476 A1* | 6/2003 | Sancoff et al. | 606/139 |
| 2004/0045418 A1* | 3/2004 | Seber et al. | 81/407 |
| 2004/0199181 A1* | 10/2004 | Knodel et al. | 606/139 |
| 2004/0260314 A1* | 12/2004 | Lizardi et al. | 606/144 |
| 2005/0165415 A1* | 7/2005 | Wales | 606/139 |
| 2006/0069407 A1* | 3/2006 | Weber | 606/205 |
| 2006/0217743 A1* | 9/2006 | Messerly et al. | 606/139 |
| 2007/0169592 A1* | 7/2007 | Putsch | 81/408 |
| 2007/0225735 A1* | 9/2007 | Stone et al. | 606/144 |
| 2008/0015631 A1* | 1/2008 | Lee et al. | 606/205 |

* cited by examiner

HANDLE SYSTEM FOR SUTURE DRIVING DEVICE

FIELD OF THE INVENTION

This invention relates to handle control devices usable with medical devices, and more particularly, to handle control devices usable with suture driving medical devices.

BACKGROUND OF THE INVENTION

There exists numerous suture delivery devices for passing a suture into tissue by an arthroscopic surgeon. Some of the devices include a needle configured to pass a suture through a tissue, whereby the needle is inserted into the tissue and retracted. Other devices are configured to insert a needle into tissue and to pull the needle through the tissue to pass a suture through the tissue. Some of these designs require that a needle be positioned in the suture delivery device before each use. In addition, some of the devices do not include systems for retaining the needle in the suture delivery devices. As a result, needles often fall out of the suture delivery devices when the devices are handed from an assistant to a surgeon, when a surgeon is positioning a device for use, and in other situations. Each time a needle falls from a suture delivery device, the needle must be sterilized or replaced, thereby resulting in unnecessary time delay and expense. Thus, a need exists for a suture delivery device having a system for preventing suture delivery needles from falling out of the suture delivery device before the needle is driven through tissue.

SUMMARY OF THE INVENTION

This invention is directed to a handle system usable for controlling medical devices. In at least one embodiment, the handle system may be directed to an embodiment configured to be used with a medical device formed of a suture delivery device. The handle system may enable a suture delivery system of the suture delivery device to be retained in a partially actuated position to prevent a needle from falling out of the suture delivery device. The needle and components of the handle system may be held in position through use of a position retention arm. By preventing the needle from falling out of the suture delivery device, the efficiency and safety of a medical device to which the handle system is attached is greatly increased. In addition, surgical personnel using a medical device incorporating the handle system is able to use the medical device in any position without risk of the needle falling out of the device.

In one embodiment, the handle system may be formed from a handle body configured to be received in a human hand. The handle system may also include a jaw operating arm pivotably coupled to the handle body at a first end and biased away from the handle body. A needle drive shaft controlling arm may be pivotably coupled to the handle body and biased away from the handle body. The needle drive shaft controlling arm may be pivotably coupled to the handle body at an end of the handle body that is generally opposite to an end of the handle body to which the jaw operating arm is attached. In at least one embodiment, the biasing of the jaw operating arm may be weaker than, or less than, the biasing of the needle drive shaft controlling arm. The needle drive shaft controlling arm may also include a needle drive shaft attachment device. The needle drive shaft attachment device may, in at least one embodiment, be formed from at least one pin extending from the needle drive shaft controlling arm and configured to be received within a slot on a head of the needle drive shaft, or vice versa.

A position retention arm may be pivotably coupled to the needle drive shaft controlling arm and slideably coupled to the handle body. The position retention arm may be positioned to retain the handle system in a partially actuated position to prevent the needle from falling from a suture delivery device. The position retention arm may be coupled to the handle body between a location where the needle drive shaft controlling arm is pivotably coupled to the handle body and a location wherein the jaw operating arm is attached to the handle body. In one embodiment, the position retention arm may include at least one slot receiving a pin extending from the handle body. The slot may include a first section that facilitates movement of a needle drive shaft generally along a longitudinal axis of the needle drive shaft and a second section of the slot that facilitates movement of the needle drive shaft generally along the longitudinal axis. The first and second sections of the slot may be separated by a retention device that prevents the pin from inadvertently passing from the second section to the first section. The retention device may include a section of the slot having a longitudinal axis that is less than 90 degrees relative to an axis extending between a pivot point on the needle drive shaft controlling arm and a pin on the handle body. In one embodiment, the longitudinal axis of the retention device may positioned greater than or equal to 85 degrees and less than 90 degrees, and may be positioned at 87 degrees. Such a configuration prevents the needle drive shaft from being moved to a starting position that would enable a needle to fall out.

The handle system may also include a movement transfer device for transferring movement from the jaw operating arm to a jaw actuating shaft to operate a tissue grasping device. The movement transfer device may be formed from a transfer arm pivotably mounted to the handle body and configured to engage a slidable jaw actuating shaft and to engage the jaw operating arm. The transfer arm may include a slot in the transfer arm adapted to receive a pin extending from the slidable jaw actuating shaft. The transfer arm may include one or more teeth, such as two teeth, extending from the transfer arm to engage the jaw operating arm. The jaw operating arm may include at least one tooth extending from the jaw operating arm to engage at least one tooth extending from the transfer arm.

During use, the handle system together with a suture delivery device may be used to insert a needle and a suture into a material, such as tissue. A needle may be inserted into a needle insertion slot in a suture delivery device. The needle drive shaft may be advanced toward the tissue grasping device to advance the needle into a needle delivery channel. The needle drive shaft may be advanced by advancing the needle drive shaft controlling arm until the retention device on the position retention arm is secured. By inserting the needle into the needle delivery channel, the needle is prevented from falling out of the suture delivery device. In addition, the needle drive shaft may be held in this position using the retention device, which prevents the needle drive shaft from returning to the starting position. In this retained position, the suture delivery device may be turned in numerous manners without risk that the needle will fall out of the needle insertion slot.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 1:
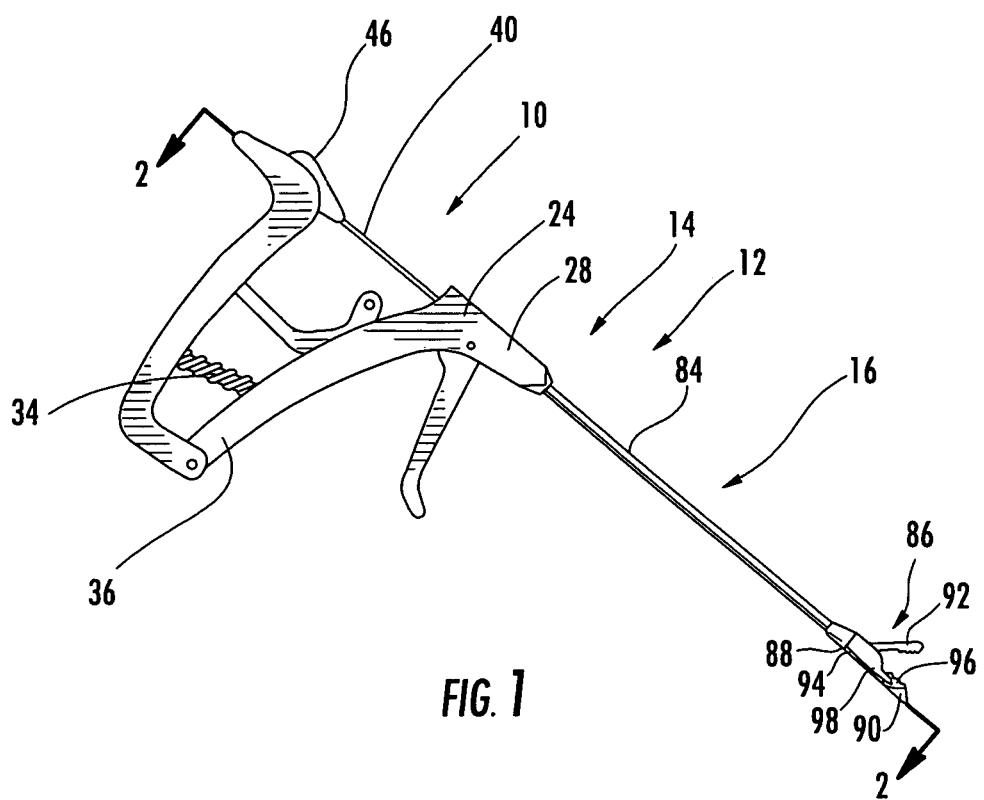
FIG. 1 is a perspective view of a suture delivery device having aspects according to the invention.
Figure 2:
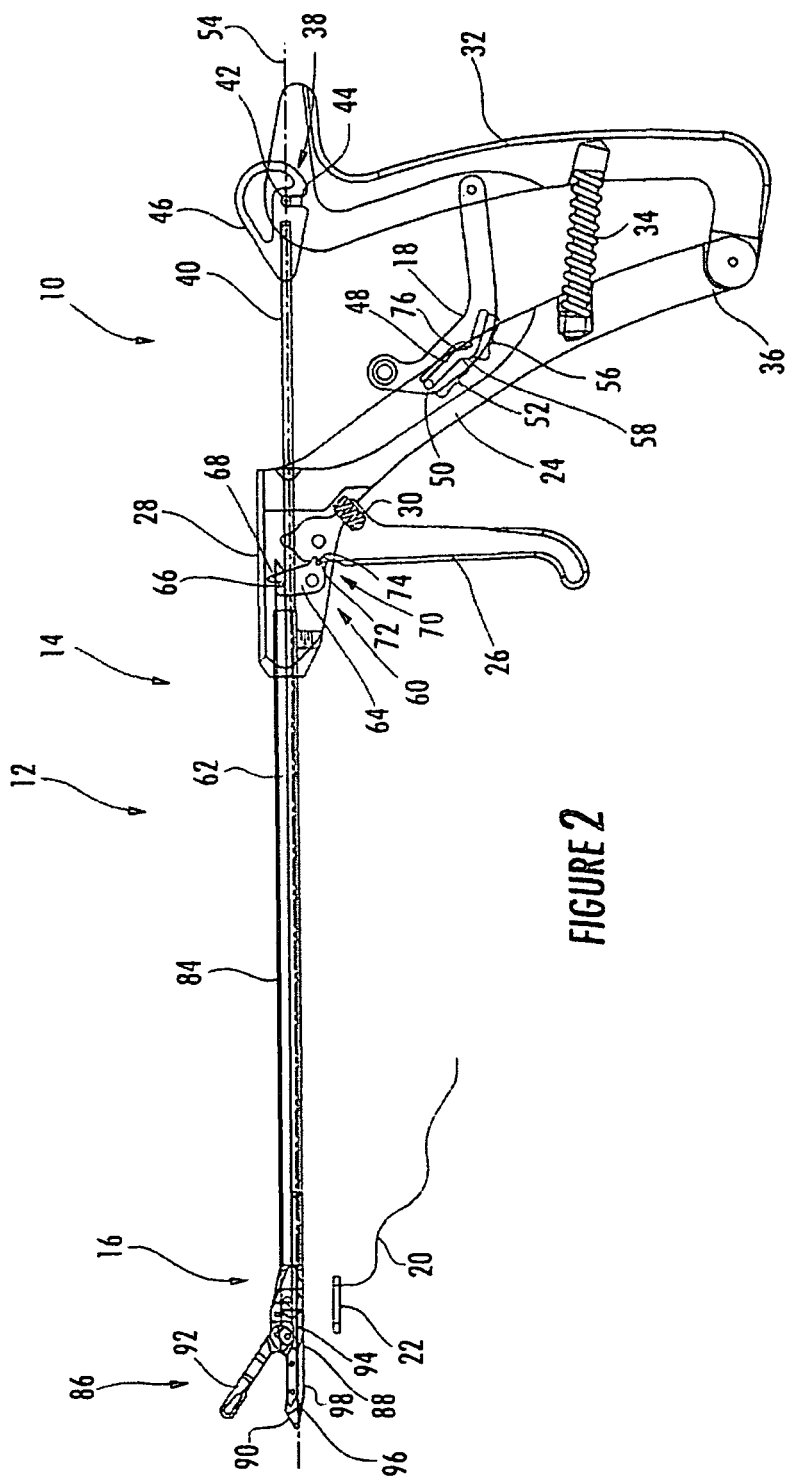
FIG. 2 is a cross-sectional side view of the suture delivery device shown in FIG. 1 taken at section line 2-2.
Figure 3:
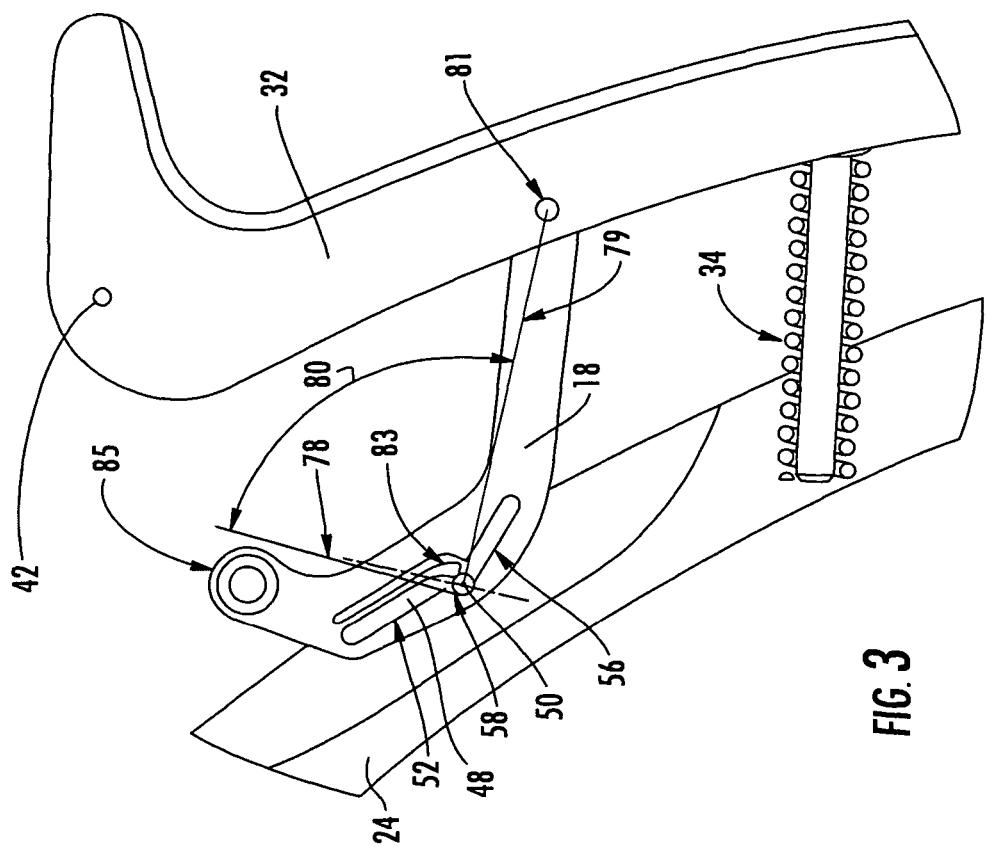
FIG. 3 is a partial cross-sectional view of the suture delivery device shown FIG. 2.

This invention, as shown in FIGS. 1-3, is directed to a handle system 10 usable for controlling medical devices 12. In at least one embodiment, the handle system 10 may be directed to an embodiment configured to be used with a medical device 12 formed of a suture delivery device 14. The handle system 10 may enable a suture delivery system 16 of the suture delivery device 14 to remain in a partially actuated position through use of a position retention device 18, such as a position retention arm. By enabling the suture delivery system 16 to be held in a partially actuated position, a suture 20 and needle 22 coupled to the suture 20 are prevented from being dislodged from suture delivery system 16. Such handle system 10 thereby increases the efficiency and safety of a medical device 12 to which the handle system 10 is attached.

As shown in FIGS. 1 and 2, the handle system 10 may be formed from a handle body 24 configured to be received in a human hand. The handle body 24 may have any configuration necessary to fit comfortably within the grasp of a human hand. The handle system 10 may include a jaw operating device 26, such as a jaw operating arm. The jaw operating arm 26 may be pivotably coupled to the handle body 24 at a first end 28. The jaw operating arm 26 may be biased away from the handle body 24. In at least one embodiment, the jaw operating arm 26 may be biased with a spring 30 extending between the jaw operating arm 26 and the handle body 24. The jaw operating arm 26 may be configured to be engaged by fingers of a human hand to actuate the jaw operating arm 26.

The handle system 10 may also include a needle acutation device 32, such as a needle drive shaft controlling arm, pivotably coupled to the handle body 24. The needle drive shaft controlling arm 32 may be configured to fit into the palm of a human hand. The needle drive shaft controlling arm 32 may also be biased away from the handle body. In at least one embodiment, as shown in FIG. 2, the needle drive shaft controlling arm 32 may be biased with a spring 34 positioned between the needle drive shaft controlling arm 32 and the handle body 24. As shown in FIG. 2, the needle drive shaft controlling arm 32 may extend from an end 36 of the handle body 24 that is generally opposite to the first end 28 to which the jaw operating arm 26 is attached.

A needle drive shaft attachment device 38 may be attached to an end of the needle drive shaft controlling arm 32, as shown in FIG. 2. The needle drive shaft attachment device 38 may be configured to be attached to a needle drive shaft 40. In at least one embodiment, the needle drive shaft attachment device 38 may include one or more pins 42 extending from the needle drive shaft controlling arm 32 and configured to be received within a slot 44 on a head 46 of the needle drive shaft 40. The slot 44 enables the pin 42 to move and remain within the slot 44 as the needle drive shaft 40 is moved generally along a longitudinal axis 54 of the needle drive shaft 40. The needle drive shaft attachment device 38 is not limited to this configuration. Rather, the needle drive shaft attachment device 38 may have other appropriate configurations.

The needle drive shaft controlling arm 32 may also include a position retention arm 18 pivotably coupled to the needle drive shaft controlling arm 32 and slideably coupled to the handle body 24. The position retention arm 18 may be configured to control movement of the needle drive shaft controlling arm 32 relative to the handle body 24. In at least one embodiment, the position retention arm 18 may include a retention device 58 for preventing the needle drive shaft 40 from moving from a partially actuated position. The position retention arm 18 may include one or more slots 48 receiving a pin 50 extending from the handle body 24. The slot 48 may include a first section 52 that facilitates movement of a needle drive shaft 40 generally along the longitudinal axis 54 of the needle drive shaft 40 and a second section 56 of the slot 48 that facilitates movement of the needle drive shaft 40 generally along the longitudinal axis 54.

The first and second sections 52, 56 of the slot 48 may be separated by a retention device 58 that prevents the pin 50 from inadvertently passing from the second section 56 to the first section 52. The retention device 58, as shown in FIG. 3, may include a retention section 76 of the slot 48 having a longitudinal axis 78 that is at an angle 80 of between greater than or equal to 85 degrees and less than about 90 degrees. Angle 80 is the angle of the longitudinal axis 78 relative to an axis 79, which extends between pivot point 81 and the pin 50. The retention device 58 may also include a spring arm 83 to snap the pin 50 into a mid position when the position retention arm 18 is moved such that the pin 50 is moved from the first section 52 of the slot 48 to the second section 56 of the slot 48. The spring arm 83 may extend generally parallel to the first section 52 of the slot 48 and generally parallel to the longitudinal axis 78 of the retention section 76. The spring arm 83 may form a portion of the first section 52 of the slot 48. Before the handle system 10 is used, the retention device 58 keeps the first section 52 in a mid position, as shown in FIG. 3, which prevents a needle 22 from falling out of the medical device 12.

The handle system 10 may also include a movement transfer device 60 for attaching the jaw operating arm 26 to a slidable jaw actuating shaft 62. The movement transfer device 60 may be formed from a transfer arm 64 pivotably mounted to the handle body 24 and configured to engage the slidable jaw actuating shaft 62 and to engage the jaw operating arm 26. The transfer arm 64 may include a slot 66 adapted to receive a pin 68 extending from the slidable jaw actuating shaft 62. The transfer arm 64 may also include a power transfer mechanism 70 for transferring movement from the jaw operating arm 26 to the transfer arm 64. The transfer arm 64 enables movement in a first direction to be transferred to the jaw actuating shaft 62 in an opposite direction. The power transfer mechanism 70 may, in at least one embodiment, be formed from one or more teeth 72, such as two teeth, extending from the transfer arm 64 to engage the jaw operating arm 26. The teeth 72 may engage one or more teeth 74 extending from the jaw operating arm 26. The transfer arm 64 may be configured such that such that as the jaw operating arm 26 is moved towards the handle body 24, the jaw actuating shaft 62 is advanced generally along the longitudinal axis 54 of the needle drive shaft 40 and away from the handle body 24.

In at least one embodiment, as shown in FIGS. 1 and 2, the handle system 10 may be coupled to a suture delivery device 14. The suture delivery device 14 may include a shaft housing 84 extending from the handle body 24. The suture delivery device 14 may also include a tissue grasping device 86 coupled to the shaft housing 84 at an end 88 generally opposite to the handle body 24 and formed from a lower jaw 90 and an upper jaw 92 pivotably coupled to the shaft housing 84 proximate to the lower jaw 90. A jaw actuating shaft 62 may extend from the handle body 24 through the shaft housing 84 and be coupled to the tissue grasping device 86. A needle drive shaft 40 may also be positioned in the shaft housing 84. The suture delivery device 14 may also include a needle insertion slot 94 in the shaft housing 84 that is coupled to a needle delivery channel 96. The needle delivery channel 96 may include a slot 98 configured to allow a suture 20 to extend from a needle 22 positioned in the channel 96.

During use, the handle system 10 together with the suture delivery device 14 may be used to insert a needle 22 and a suture 20 into a material, such as tissue. A needle 22 may be inserted into the needle insertion slot 94. The needle drive shaft 40 may be advanced toward the tissue grasping device 86 to advance the needle 22 into the needle delivery channel 96. The needle drive shaft 40 may be advanced by advancing the needle drive shaft controlling arm 32 until the retention device 58 on the position retention arm 18 is secured. By inserting the needle 22 into the needle delivery channel 96, the needle 22 is prevented from falling out of the suture delivery device 14. In addition, the needle drive shaft 40 may be held in this position using the retention device 58, which prevents the needle drive shaft 40 from returning to the starting position. In this retained position, the suture delivery device 14 may be turned in numerous manners without the possibility that the needle 22 will fall out of the needle insertion slot 94.

Once the needle 22 is properly positioned in the needle drive shaft 40, the tissue grasping device 86 may be used to grasp tissue, such as animal or human tissue or other material, to insert the needle 22 and suture though the tissue. As shown in FIGS. 1 and 2, the tissue grasping device 86 may be formed from a lower jaw 90 and an upper jaw 92. The tissue grasping device 86 may be actuated by grasping the handle system 10 by placing the needle drive shaft controlling arm 32, the handle body 24 and the jaw operating arm 26 in a human hand. The device 14 may be actuated by squeezing the handle system 10. In at least one embodiment, the spring 30 attached to the jaw operating arm 26 may be weaker than the spring 34 attached to the needle drive shaft controlling arm 32. Thus, once the handle system 10 is squeezed, the jaw operating arm 26 moves first until the tissue grasping device 86 grasps tissue. The jaw operating arm 26 may move the actuating shaft 62 by transferring movement through the transfer arm 64. As the jaw operating arm 26 is moved towards the handle body 24, the transfer arm 64 rotates clockwise. The clockwise movement of the transfer arm 64 pulls the jaw actuating shaft 62 away from the tissue grasping device 86. The linkages in the tissue grasping device 86 transfer the movement to cause an upper jaw 92 to be moved toward the lower jaw 90 to close the tissue grasping device 86.

The needle drive shaft controlling arm 32 may then be advanced toward the handle body 24. Advancing the drive shaft controlling arm 32 causes the needle drive shaft 40 to be advanced in the shaft housing 84 and causes the needle 22 to be pushed through the needle delivery channel 96. In at least one embodiment, needle delivery channel 96 may be curved and cause the needle 22 to be bent while being moved through the needle delivery channel 96.

Releasing pressure on the needle drive shaft control arm 32 enables the needle drive shaft control arm 32 to move into a mid position, as shown in FIG. 3. In particular, releasing pressure on the needle drive shaft control arm 32 causes the pin 50 to move through the first section 52 and snap into the retention device 58 in contact with the spring arm 83. The retention device 58 may be released by applying a force to the handle 85 to move the pin 50 through the retention device 58 and into the second section 56 of the slot 48.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A handle for a suture delivery device, comprising:
a handle body configured to be received in a human hand;
a jaw operating arm pivotably coupled to the handle body at a first end and biased away from the handle body;
a needle drive shaft controlling arm pivotably coupled to the handle body and biased away from the handle body;
a position retention arm pivotably coupled to the needle drive shaft controlling arm and slideably coupled to the handle body;
wherein the position retention arm includes at least one slot receiving a pin extending from the handle body; and
wherein the at least one slot includes a first slot section that facilitates movement of a needle drive shaft generally along a longitudinal axis of the needle drive shaft and a second slot section of the at least one slot that facilitates movement of the needle drive shaft generally along the longitudinal axis;
wherein the first and second slot sections of the at least one slot are separated by a retention slot section and a spring arm that contacts the pin and extends generally parallel to the first slot section and generally parallel to the retention slot section, whereby the spring arm retains the pin in the retention slot section and prevents the pin from inadvertently passing from the second slot section to the first slot section;
wherein the first slot section is positioned oblique to the retention slot section;
wherein the retention slot section is positioned oblique to the second slot section, whereby a needle is retained within the suture delivery device when the pin is retained in the retention slot section; and
wherein the first slot section is defined in part by the spring arm and in part by the position retention arm, and the second slot section is defined by the position retention arm.

2. The handle of claim 1, further comprising a movement transfer device formed from a transfer arm pivotably mounted to the handle body and configured to engage a slidable jaw actuating shaft and to engage the jaw operating arm.

3. The handle of claim 2, further comprising a slot in the transfer arm adapted to receive a pin extending from the slidable jaw actuating shaft.

4. The handle of claim 2, further comprising at least one tooth extending from the transfer arm to engage the jaw operating arm.

5. The handle of claim 4, further comprising at least one tooth extending from the jaw operating arm to engage the at least one tooth extending from the transfer arm.

6. The handle of claim 1, wherein the bias on the jaw operating arm is less than the bias on the needle drive shaft controlling arm enabling the jaw operating arm to move first when the jaw operating arm and the needle drive shaft controlling arm are positioned in a hand and squeezed.

7. The handle of claim 1, wherein the jaw operating arm is spring biased away from the handle body.

8. The handle of claim 1, wherein the needle drive shaft controlling arm is spring biased away from the handle body.

9. The handle of claim 1, wherein the needle drive shaft controlling arm is pivotably coupled to an end of the handle body that is generally opposite to an end of the handle body to which the jaw operating arm is attached.

10. The handle of claim 9, wherein the position retention arm is positioned on the handle body between a location where the needle drive shaft controlling arm is pivotably coupled to the handle body and a location wherein the jaw operating arm is attached to the handle body.

11. The handle of claim 1, wherein the needle drive shaft controlling arm further comprises a needle drive shaft attachment device.

12. The handle of claim 11, wherein the needle drive shaft attachment device comprises at least one pin extending from the needle drive shaft controlling arm and configured to be received within a slot on a head of the needle drive shaft.

13. The handle of claim 1, wherein the retention slot section comprises a section of the at least one slot having a longitudinal axis that is at an angle of greater than about 85 degrees and less than about 90 degrees relative to an axis extending between a pivot on the needle drive shaft controlling arm and the pin extending from the handle body.

14. A handle for a suture delivery device, comprising:
a handle body configured to be received in a human hand;
a jaw operating arm pivotably coupled to the handle body at a first end and biased away from the handle body;
a movement transfer device formed from a transfer arm pivotably mounted to the handle body and configured to engage a slidable jaw actuating shaft and to engage the jaw operating arm such that as the jaw operating arm is moved towards the handle body, the jaw actuating shaft is advanced along a longitudinal axis of the jaw actuating shaft and away from the handle body;
a needle drive shaft controlling arm pivotably coupled to the handle body at a second end of the handle body that is generally opposite to the first end, wherein the needle drive shaft controlling arm is biased away from the handle body;
a position retention arm pivotably coupled to the needle drive shaft controlling arm, slideably coupled to the handle body, and positioned on the handle body between a location where the needle drive shaft controlling arm is pivotably coupled to the handle body and a location wherein the jaw operating arm is attached to the handle body;
wherein the position retention arm includes at least one slot receiving a pin extending from the handle body; and
wherein the at least one slot includes a first slot section that facilitates movement of a needle drive shaft generally along a longitudinal axis of the needle drive shaft and a second slot section of the at least one slot that facilitates movement of the needle drive shaft generally along the longitudinal axis;
wherein the first and second slot sections of the at least one slot are separated by a retention slot section and a spring arm that contacts the pin and extends generally parallel to the first slot section and generally parallel to the retention slot section, whereby the spring arm retains the pin in the retention slot section and prevents the pin from inadvertently passing from the second slot section to the first slot section;
wherein the first slot section is positioned oblique to the retention slot section;
wherein the retention slot section is positioned oblique to the second slot section, whereby a needle is retained within the suture delivery device when the pin is retained in the retention slot section; and
wherein the first slot section is defined in part by the spring arm and in part by the position retention arm, and the second slot section is defined by the position retention arm.

15. The handle of claim 14, further comprising a slot in the transfer arm adapted to receive a pin extending from the slidable jaw actuating shaft and at least one tooth extending from the transfer arm to engage at least one tooth extending from the jaw operating arm.

16. The handle of claim 14, wherein the bias on the jaw operating arm is less than the bias on the needle drive shaft controlling arm enabling the jaw operating arm to move first when the jaw operating arm and the needle drive shaft controlling arm are positioned in a hand and squeezed.

17. The handle of claim 14, wherein the needle drive shaft controlling arm further comprises a needle drive shaft attachment device comprising at least one pin extending from the needle drive shaft controlling arm and configured to be received within a slot on a head of the needle drive shaft.

18. A suture delivery device, comprising:
a handle body configured to be received in a human hand;
a shaft housing extending from the handle body;
a tissue grasping device coupled to the shaft housing at an end generally opposite to the handle body and formed from a lower jaw and an upper jaw pivotably coupled to the shaft housing proximate to the lower jaw;
a jaw actuating shaft coupled to the tissue grasping device and extending to the handle body;
a needle drive shaft positioned in the shaft housing;
a jaw operating arm pivotably coupled to the handle body at a first end, engaged to the jaw actuating shaft, and biased away from the handle body;
a movement transfer device formed from a transfer arm pivotably mounted to the handle body and configured to engage the jaw actuating shaft and to engage the jaw operating arm such that as the jaw operating arm is moved towards the handle body, the jaw actuating shaft is advanced along a longitudinal axis of the jaw actuating shaft and away from the handle body;
a needle drive shaft controlling arm pivotably coupled to the handle body at a second end of the handle body that is generally opposite to the first end, wherein the needle drive shaft controlling arm is biased away from the handle body;
a position retention arm pivotably coupled to the needle drive shaft controlling arm, slideably coupled to the handle body, and positioned on the handle body between a location where the needle drive shaft controlling arm is pivotably coupled to the handle body and a location wherein the jaw operating arm is attached to the handle body;
wherein the position retention arm includes at least one slot receiving a pin extending from the handle body; and
wherein the at least one slot includes a first slot section that facilitates movement of a needle drive shaft generally along a longitudinal axis of the needle drive shaft and a second slot section of the at least one slot that facilitates movement of the needle drive shaft generally along the longitudinal axis;
wherein the first and second slot sections of the at least one slot are separated by a retention slot section and a spring arm that contacts the pin and extends generally parallel to the first slot section and generally parallel to the retention slot section, whereby the spring arm retains the pin in the retention slot section and prevents the pin from inadvertently passing from the second slot section to the first slot section;
wherein the first slot section is positioned oblique to the retention slot section;
wherein the retention slot section is positioned oblique to the second slot section, whereby a needle is retained within the suture delivery device when the pin is retained in the retention slot section; and wherein the first slot section is defined in part by the spring arm and in part by the position retention arm, and the second slot section is defined by the position retention arm.

19. The handle of claim 18, further comprising a slot in the transfer arm adapted to receive a pin extending from the slidable jaw actuating shaft and at least two teeth extending from the transfer arm to engage at least one tooth extending from the jaw operating arm.

20. The handle of claim 18, wherein the bias on the jaw operating arm is less than the bias on the needle drive shaft controlling arm enabling the jaw operating arm to move first when the jaw operating arm and the needle drive shaft controlling arm are positioned in a hand and squeezed.

21. The handle of claim 18, wherein the needle drive shaft controlling arm further comprises a needle drive shaft attachment device comprising at least one pin extending from the needle drive shaft controlling arm and configured to be received within a slot on a head of the needle drive shaft.

* * * * *